United States Patent [19]

Harréus et al.

[11] 3,984,494

[45] Oct. 5, 1976

[54] GRAFT COPOLYMERS OF VINYL ACETATE ON POLYETHYLENE OXIDE AS SELF-SUPPORTING CAPSULES

[75] Inventors: Albrecht Harréus, Kelkheim, Taunus; Wolfgang Zimmermann, Frankfurt am Main, both of Germany

[73] Assignee: Hoechst Aktiengesellschaft, Frankfurt am Main, Germany

[22] Filed: Dec. 19, 1974

[21] Appl. No.: 534,279

[30] Foreign Application Priority Data
Dec. 21, 1973 Germany............................ 2363853

[52] U.S. Cl................................ 260/874; 252/316; 264/92; 264/301; 424/22; 424/33
[51] Int. Cl.$^2$.................... C08L 31/04; B01J 13/00
[58] Field of Search ................ 260/874; 424/33, 22

[56] References Cited
UNITED STATES PATENTS

| | | | |
|---|---|---|---|
| 3,033,841 | 5/1962 | Germain | 260/874 |
| 3,218,281 | 11/1965 | Rees | 260/874 |
| 3,244,772 | 4/1966 | Von Bonin et al. | 260/874 |
| 3,630,955 | 12/1971 | Emrick | 424/33 |
| 3,674,704 | 7/1972 | Bayless et al. | 424/33 |
| 3,676,529 | 7/1972 | Fall | 260/874 |
| 3,726,803 | 4/1973 | Bayless et al. | 424/33 |

*Primary Examiner*—Murray Tillman
*Assistant Examiner*—Thurman K. Page
*Attorney, Agent, or Firm*—Curtis, Morris & Safford

[57] ABSTRACT

An encapsulating material for drugs consisting of a modified polyvinyl alcohol which is a partially hydrolized graft copolymer of vinyl acetate on polyethylene oxide.

8 Claims, No Drawings

GRAFT COPOLYMERS OF VINYL ACETATE ON POLYETHYLENE OXIDE AS SELF-SUPPORTING CAPSULES

The present invention relates to self-supporting packs or capsules for wrapping drugs.

Hitherto, medical capsules are practically exclusively manufactured from gelatine. This basis substance, despite its absolute physiological harmlessness, has certain serious disadvantages. Being a natural product, gelatine does not possess constant physical, especially mechanical properties, it is not resistant to acids and light and, above all, prone to infection by microorganisms; sterilization after such an infection is practically impossible.

Despite these disadvantages, gelatine as encapsulating material for drugs hitherto has not been replaced, although, searching for a suitable substitute, various polymers or polymer mixtures have been proposed as material for drug capsules. Japanese Patent Application Sho-45-1277, for example, describes the use of polyvinyl alcohol as basis material for capsules. The use of polyvinyl alcohol and other polymers for drug capsules is known also from German Offenlegungsschrift No. 1 965 584. However, all these substances, in industrial practice of capsule manufacturing as well as in capsule application, proved to be no perfect substitute for gelatine.

Disadvantageous for the use of polyvinyl alcohol as basis material for capsules is above all the necessity of plasticizing it by means of an external plasticizer, which plasticizer may emigrate on the one hand, and on the other may penetrate into the encapsulated drug. Especially in the case of prolonged storage of the capsules, brittleness and formation of cracks may occur as well as modification of the drugs.

It has now been found that self-supporting packs or capsules for wrapping drugs may be prepared in an especially advantageous manner from a modified polyvinyl alcohol being a partially saponified graft copolymer of vinyl acetate on polyethylene oxide which contains from 1 to 50 weight %, preferably from 20 to 30 weight %, of ethylene oxide units; from 1 to 50 weight %, preferably from 20 to 30 weight %, of vinyl acetate units; and from 20 to 98 weight %, preferably from 40 to 60 weight %, of vinyl alcohol units.

The preparation of such modified polyvinyl alcohols is described in German Patents Nos. 1 081 229 and 1 094 457.

For the preparation of the modified polyvinyl alcohol to be used according to the present invention, a polyethylene oxide having a molecular weight above 10,000, preferably from 20,000 to 25,000, is used. The viscosity of a 4 % aqueous solution of the modified polyvinyl alcohol at 20°C is in the range of from 2 to 10 cP, preferably from 2 to 5 cP.

The modified polyvinyl alcohol is physiologically harmless and practically non-toxic, it is easily soluble in water as well as in the gastric and intestinal juice. The modified polyvinyl alcohol is internally plasticized by the polyethylene oxide content, so that a migration or exudation of the plasticizer cannot occur, which is a substantial advantage over externally plasticized polyvinyl alcohol. If necessary, however, the modified polyvinyl alcohol may be plasticized additionally by means of external plasticizers such as glycerol, sorbitol, cane sugar or propyleneglycol.

The modified polyvinyl alcohol may be processed in the form of aqueous solutions to yield drug capsules according to the dip process known from the processing of gelatine. The capsules may also be molded according to known processing methods for thermoplastic materials or deep-drawn from a sheet according to the positive or negative process.

Under normal conditions, the capsules are nearly not susceptible to be attacked by microorganisms, and they may be easily sterilized in simple manner according to the processes usual in medicine.

The modified polyvinyl alcohol may be adapted to the processing conditions within a wide range by variation of the polyethylene oxide content and the saponification degree within the above mentioned limits; these conditions being for example given by the mechanical filling equipment for drug capsules. A decrease in the polyethylene oxide content or an increase of the saponification degree yields a hard material and correspondingly more rigid capsules; on the other hand, by increse of the polyethylene oxide content or decrease of the saponification degree within the cited limits a soft modified polyvinyl alcohol is obtained from which capsules of higher softness degree may be prepared.

The following examples illustrate the invention.

EXAMPLE 1

Manufacture of hard capsules according to the dip process:

A substantially foam-free clear solution was prepared by strewing 50 parts by weight of a modified polyvinyl alcohol containing 50 weight % of vinyl alcohol units
25 weight % of vinyl acetate units
25 weight % of ethylene oxide units into 50 parts by weight of cold water and heating the whole with agitation in a water bath to about 90°C. This solution was transferred into a dip trough, and some air bubbles in the solution were removed in vacuo. At 50°C, the solution had a viscosity of 170 poises, measured by means of the Hoppler falling ball viscometer.

As dipping mold, smooth iron pins rounded off at their ends and made hydrophobic by means of silicone oil were used. For better handling, 10 each of these pins were mounted onto an iron plate. In order to manufacture hard capsules consisting of two parts, dipping pins having different diameters, that is, a. of 7.2 mm for the capsule and b. of 7.7 mm for the cover were provided. The tolerance between the outer diameter of the capsule and the inner diameter of the cover depends on the wall thickness of the finished parts of the capsule and was from about 0.1 to 0.3 mm.

Both dipping molds were vertically immersed into the solution of the modified polyvinyl alcohol heated to 80°C, and subsequently dried in a drying channel at about 100°C while swinging them constantly. The time of drying was about 15 to 30 minutes; the constant movement of the mold during this time being necessary in order to obtain a uniform wall thickness. After drying, the capsule parts, that is, capsule and cover, were slipped off the corresponding pins.

EXAMPLE 2

Capsules manufactured according to the deep-drawing process:

Using the same modified polyvinyl alcohol as indicated in Example 1, a sheet having a thickness of 0.5 mm was manufactured by slot die extrusion. Sections of this sheet were introduced into a vacuum deep-drawing machine with positive mold, trade mark "Kiefel," type KL 3 AV, and the corresponding capsules and their covers were deep-drawn at a temperature of 200°C and a heating time of 15 seconds.

In a subsequent operation, the capsules were separated from excess sheet material by means of a knife.

What is claimed is:

1. Self-supporting packs or capsules for drugs, wherein the capsule material is composed of a modified polyvinyl alcohol being a partially saponified graft copolymer of vinyl acetate on polyethylene oxide which contains from 1 to 50 weight % of ethylene oxide units, from 1 to 50 weight % of vinyl acetate units, and from 20 to 98 weight % of vinyl alcohol units.

2. Self-supporting packs or capsules for drugs as claimed in claim 1 wherein the capsule material is composed of from 20 to 30 weight % of ethylene oxide units, from 20 to 30 weight % of vinyl acetate units, and from 40 to 60 weight % of vinyl alcohol units.

3. Self-supporting packs or capsules as claimed in claim 1 wherein the polyethylene oxide component of the graft copolymer has a molecular weight of at least 10,000.

4. Self-supporting packs or capsules as claimed in claim 2 wherein the polyethylene oxide component of the graft copolymer has a molecular weight of about 20,000 to 25,000.

5. A modified polyvinyl alcohol drug capsule comprising a partially saponified graft copolymer of vinyl acetate on polyethylene oxide which graft copolymer contains:
   1 to 50 weight percent ethylene oxide units, 1 to 50 weight percent vinyl acetate units, and 20 to 98 weight percent vinyl alcohol units, wherein the polyethylene oxide component of the graft copolymer has a molecular weight of at least 10,000.

6. A modified polyvinyl alcohol drug capsule consisting essentially of a partially saponified graft copolymer of vinyl acetate on polyethylene oxide which copolymer contains:
   20 to 30 weight percent of ethylene oxide units,
   20 to 30 weight percent of vinyl acetate units,
   and 40 to 60 weight percent of vinyl alcohol units, wherein the polyethylene oxide component of the graft copolymer has a molecular weight of about 20,000 to 25,000.

7. The modified polyvinyl alcohol drug capsule of claim 5 which contains about 25 weight percent of ethylene units, about 25 weight percent of vinyl acetate units, and about 50 weight percent of vinyl alcohol units.

8. The modified polyvinyl alcohol drug capsule of claim 5 wherein the capsule is water soluble.

* * * * *